United States Patent [19]

Lybrand et al.

[11] 4,003,999
[45] Jan. 18, 1977

[54] ASPIRIN-TEA COPRECIPITATES FOR TREATING INFLAMMATION

[75] Inventors: Robert Archie Lybrand, Ashland; Louis Gary Bell, Richmond, both of Va.

[73] Assignee: A. H. Robins Company, Incorporated, Richmond, Va.

[22] Filed: May 8, 1975

[21] Appl. No.: 575,898

Related U.S. Application Data

[63] Continuation-in-part of Ser. No. 404,945, Oct. 10, 1973, abandoned, which is a continuation-in-part of Ser. No. 300,796, Oct. 25, 1972, abandoned.

[52] U.S. Cl. .............................. 424/195; 424/230; 424/231
[51] Int. Cl.² ................. A61K 31/60; A61K 35/78
[58] Field of Search .................. 424/195, 230, 231

[56] References Cited

UNITED STATES PATENTS 1,486,373   3/1924   Gerngross et al. ................ 424/330

OTHER PUBLICATIONS

*Journal of the Amer. Pharm. Assoc.,* vol. 42, pp. 138–145; vol. 43, pp. 527–530 (1953 & 1954).
*The Dispensatory of the U.S.A.,* 24th Ed. (1947), pp. 16–19, 1204–1207 & 1624–1624.
Husa's "Pharmaceutical Dispensing", 5th Ed., (1959), pp. 427–431 & 460–463.
*Chem. Abst.,* vol. 61–14475n, vol. 65–11146a, vol. 65–4263g, vol. 59–6909e.

*Primary Examiner*—Stanley J. Friedman

[57] ABSTRACT

A novel coprecipitate of aspirin and tea is described. The coprecipitate is prepared by acidification of a solution of aspirin and tea. In vivo pharmacological evaluation of the coprecipitate shows that the therapeutic activity of aspirin has been retained and the side effects commonly associated with aspirin such as irritation of the gastric mucosa, bleeding and ulceration have been markedly reduced.

24 Claims, No Drawings

ASPIRIN-TEA COPRECIPITATES FOR TREATING INFLAMMATION

The present application is a continuation-in-part application of application Ser. No. 404,945 filed Oct. 10, 1973 now abandoned, which was a continuation-in-part application of copending application Ser. No. 300,796 filed Oct. 25, 1972, and now abandoned.

The present invention relates to anti-inflammatory compositions and is more particularly concerned with certain coprecipitates of tea and aspirin which retain the anti-inflammatory activity of aspirin and prevent gastric irritation, bleeding and ulceration, therapeutic compositions containing said coprecipitates as active ingredients and methods for the preparation of said coprecipitates.

It has long been known that orally administered aspirin often causes gastric irritation and in some instances bleeding and ulceration in warm-blooded animals. Undispersed particles of aspirin may lodge in the folds of the stomach tissue or may adhere to the surface of tissue or there may be insufficient liquids to suspend the aspirin. These conditions may lead quickly to gastric lesions and bleeding. Aspirin may be particularly damaging to certain individuals who require large dosages and treatment for extended periods of time. Attempts to reduce gastric irritation have been made by combining aspirin with aluminum and magnesium adjuncts or by other buffering materials and the efficacy of such combinations has not been fully determined and is still the subject of medical debate. Reduced gastric irritation has been reported using aspirincaseinate by Feinblatt, T. M. and Ferguson, E. A., "Aspirin-Caseinate in Patients with Gastric Sensitivity to Plain Aspirin," New York State Journal of Medicine, Vol. 63 (19), Oct. 1, 1963, p2805–2807.

Coprecipitates of lignosulfonate and anti-inflammatory compounds which have been shown to possess a high degree of anti-inflammatory activity and which prevent gastric irritation are the subject of copending application Ser. No. 459,828 filed Apr. 10, 1974, now abandoned which was a continuation-in-part application of copending application Ser. No. 271,986 filed July 14, 1972, now abandoned, which was a continuation-in-part of copending application Ser. No. 89,999, now abandoned.

Coprecipitates of tannic acid and anti-inflammatory compounds which have been shown to possess a high degree of anti-inflammatory activity and which prevent gastric irritation are the subject of application Ser. No. 345,802 filed Mar. 3, 1973, now abondoned, which was a continuation application of copending application Ser. No. 189,040, now abandoned.

In general, naturally occurring tannins have been classified into two groups, (a) hydrolyzable tannins which are esters of sugar, usually glucose with one or more trihydroxybenzene carboxylic acids, and (b) derivatives of flavanols, so called condensed tannins. (The Merck Index, 8th Ed. p. 1012, Publ. by Merck & Co., Inc., Rahway, N.J.). It is the first mentioned group (a) to which tannic acid belongs and it is the second mentioned group (b) with which the present invention is concerned, i.e., the unhydrolyzable flavanol based tannins and oxidized tannins of tea.

The present invention is based on the discovery that coprecipitates can be readily prepared from tea infusions or instant tea solutions and aspirin, that the therapeutic activity of the aspirin moiety of said coprecipitate when it is administered orally to warm-blooded animals is retained and that said coprecipitates are especially effective in preventing gastric irritation, ulceration and bleeding of the gastric mucosa frequently attendant to the oral administration of aspirin alone.

The term "tea" as used hereinafter refers to the soluble portion of the tea plant, said portion containing the flavanol based tannins and products usually resulting from the curing of said plant and the preparation of spray dried soluble extracts.

Among the tea plants which can provide a source for the condensed tannins which form a coprecipitate with aspirin are plants of the species *Camelia sinesis* and *Camelia assamica* and various intergrades between sinesis and assamica.

By the term "tea constituent" is meant the sum of materials in the coprecipitate having their derivation in the leaves and stems of the tea plant and in the fermentation thereof. The tea constituent is comprised primarily of tea tannin.

When after the preparation of a hot infusion from the leaves and stems of a tea plant containing flavanol based tannins which is suitabe for preparing a drinkable potion, said infusion is cooled, a precipitate usually forms which is generally referred to as a cream well known in the art as a "tea cream." The tea cream is mainly a complex between caffeine and certain tannin materials such as theaflavins and thearubigins which are the products of enzymatic oxidation which occurs during the curing of leaves and stems of plants. The theaflavins and thearubigins form a major part of the total tannin materials which are suitable for preparing the coprecipitates with aspirin of this invention. The tannins in the tea cream together with some tannins which remain in the original infusion are referred to as tea tannin. Further, it has been found that in order to incorporate these tannin materials into the coprecipitate, it is necessary that they be in a soluble form such as that known to the art as solublized tea cream and which can be produced by treating the tea cream with oxygen, ozone, or hydrogen peroxide, as for example, by the method of U.S. Pat. No. 3,151,985 which describes a process for the preparation of these tea tannins for use in instant teas.

Various instant teas can be used in practising the present invention, the preferred instant teas being those prepared by extracting black tea leaf (*Camelia sinesis*) with hot ater, cooling to precipitate tea cream, filtering off the tea cream and solublizing it by oxidation of the contained tea tannin and adding it back to the filtrate, concentrating the filtrate and drying.

Black teas suitable for obtaining the infusions and instant teas used in the preparation of coprecipitates of this invention are those obtained by natural fermentation processes or may be obtained as taught by U.S. Pat. No. 3,484,246.

The novel coprecipitates of the present invention are prepared utilizing tea tannin derived from the tea plant. Thus, coprecipitates can be prepared from (a) solutions of aspirin and instant tea, (b) solutions of aspirin and solublized tea cream, (c) solutions of aspirin and dairy tea (dairy tea is tea from which insoluble tea cream has been removed), (d) solutions of aspirin and decaffeinated instant tea and (e) solutions of aspirin and tea infusions. While all of the foregoing coprecipitates can be readily prepared and used in practising the present invention, the preferred coprecipitates are those made from instant tea and decaffeinated instant tea which instant teas contain all of the tea tannin and oxidized tannin. The tea moiety of the novel coprecipitates is comprised almost exclusively of tea tannin. The coprecipitates contain from about 10 to about 16% of the tea used in preparing the coprecipitates. Thus, in the novel coprecipitates of the present invention there is from about 30 to about 50% of available tea tannin initially present in the tea solution used to prepare the coprecipitates.

The coprecipitates contain small amounts of caffeine when teas containing caffeine are used but said caffeine is not necessary to the phenomenon observed with the coprecipitate of the present invention in the protection against ulceration and bleeding caused by aspirin as shown by Examples 7 and 9 wherein said coprecipitates are caffeine free.

The novel aspirin-tea coprecipitates of the present invention are not simple mixtures of aspirin and tea as is readily shown by the water-insolubility of the coprecipitates which have been isolated from their reaction mixture by filtration. After repeated water washings of the aspirin-tea coprecipitate at 25° C., the dried coprecipitate has the same analysis within experimental error. The washing of simple mixtures of aspirin and tea at 25° C. results in solution of the tea portion of the mixture, leaving the aspirin portion as a solid residue. Analysis shows the residue to be aspirin with a very small amount of salicylic acid present. The aspirin residue is equivalent within experimental error to the amount used to prepare the aspirin-tea mixture. The substance of the foregoing is exemplified as follows:

|  | Analysis before water wash | | Analysis after water wash | |
|---|---|---|---|---|
|  | Sample 250–015 | Mixture | Sample 250–015 | Mixture |
| Aspirin | 92.30 | 92.30 | 93.90 | 98.30 |
| Salicylic Acid | 0.30 | 0.00 | 0.30 | 0.20 |
| Tea Constituent | 5.70 | 7.70 | 5.40 | 0.00 |
| Water | 1.70 | 0.00 | 0.40 | 0.40 |
|  | Sample 250–021 | Mixture | Sample 250–021 | Mixture |
| Aspirin | 94.90 | 94.70 | 93.70 | 100.00 |
| Salicylic Acid | 0.20 | 0.00 | 0.20 | 0.10 |
| Tea Constituent | 4.20 | 5.30 | 5.30 | 0.00 |
| Water | 0.70 | 0.00 | 0.80 | 0.60 |

Tea constituent analysis calculated by difference. Samples 250–015 and 250–021 (Examples 11 and 12) washed with 10 vol. of water to 1 vol. of sample. Mixtures washed with 5:1 weight ratio water to sample.

The foregoing comparison demonstrates the difference in physical characteristic of the coprecipitate of aspirin and tea constituent and a mixture of aspirin and tea, the tea constituent of the coprecipitate being substantially non-leachable with water at 25° C. The tea portion was separated from the coprecipitates of other samples of Examples 11 and 12 by extracting out the aspirin with chloroform. The tea portion so isolated when used in a simple mechanical mixture with aspirin in a leaching test was readily leached away from the aspirin with water as in the above test. This portion formed an insoluble precipitate when mixed with gelatin solution and formed a green color when treated with 100 times its weight of 1% ferric nitrate solution.

The novel aspirin-tea coprecipitates can contain from 2–15% tea constituent and from 85–98% aspirin. The preferred coprecipitates contain 4–10% tea constituent and 90–96% aspirin. The percentages are weight percentages. Novel spray dried reaction residues comprised of aspirin-tea coprecipitate and reaction salts are also part of this invention.

It is, therefore, a primary object of the present invention to provide novel coprecipitates of aspirin and tea. A further object is to provide novel coprecipitates of aspirin and tea useful for the alleviation of distress caused by inflamed tissue. A still further object is to provide novel coprecipitates of aspirin and tea useful for the alleviation of distress caused by inflamed tissue and having minimal side effects. Another object is to provide methods whereby coprecipitates of aspirin and tea useful in the treatment of inflamed tissue can be prepared. Other objects will be readily apparent to one skilled in the art and still other objects will become apparent hereinafter.

The foregoing and additional objects are accomplished by the provision of novel coprecipitates of aspirin and tea. The coprecipitates are of particular interest in that they retain the valuable therapeutic activity of aspirin and have minimal side effects.

The novel aspirin-tea coprecipitates of the present invention can be prepared by acidifying an aqueous solution of a salt of acetylsalicylic acid (aspirin) and tea under controlled conditions. Aqueous aspirin-salt (e.g., sodium acetylsalicylate) solutions are prepared by dissolving acetylsalicylic acid in contact with a basic solution. Illustrative of the bases which can be used to form the salts are the alkali metal hydroxides and carbonates, calcium and ammonium hydroxides and carbonates, sodium citrate and sodium acetate. Preferably sodium carbonate is used. The acids which can be used include strong acids such as hydrochloric acid, sulfuric acid and phosphoric acid and weak acids such as glacial acetic, aqueous acetic, citric and lactic acid. Glacial acetic acid is the preferred acid. The process can be carried out at a temperature of from −2° C. to about 25° C., the preferred temperature being from about 0° C. to about 10° C.

A general procedure for preparing the novel coprecipitates of the present invention is as follows.

An aqueous basic solution is prepared by dissolving an alkali metal carbonate in water. Aspirin in approximately a stoichiometric amount is added to the cooled (2°–12° C.) solution with stirring until complete dissolution. The pH of the solution is less than 7, but can be on the basic side if excess base is added. The carbon dioxide formed is substantially eliminated during dissolution. Solid instant tea or a tea solution is added. Antifoaming agent may be added to reduce foaming. One suitable antifoaming agent is Dow Corning antifoam FG-10 emulsion food grade defoamer which has as its active primary ingredient dimethylpolysiloxane. To the cold (2°–12° C.) stirred solution is added an aliquot of the total amount of acid, preferably glacial acetic acid, and stirring continued before further acid addition. pH of the solution during this waiting period is about 3.7 to 4.2. The remainder of the acid is added gradually, the pH of the reaction mixture during this gradual addition being about 3.5 to 4.2. The macrocrystalline appearance of the coprecipitate is generally spherical and tends to be a rosette type crystal as compared to the sharp angular crystals of aspirin. After the coprecipitate has been formed it is allowed to settle from the reaction mixture, the supernatant liquid is decanted and the coprecipitate is collected by filtration. The coprecipitate is washed to eliminate reaction liquor. Water, glycine buffer solution (pH 2.6) or acid washes having a pH of about 3 can be satisfactorily used. Any aqueous wash which does not cause precipitation of residual solubilized aspirin or contaminate the product may be used. The coprecipitate is air dried to a constant weight.

In a preferred procedure a cold (0°–10° C.) solution is prepared by adding sodium carbonate and aspirin to distilled water with stirring until all solids have been dissolved. Instant tea is then added with stirring until the tea has dissolved (Solution A). A portion of Solution A is added to cold (0°–10° C.) distilled water followed by an aliquot of the total amount of glacial acetic acid used in the procedure. After stirring the initial mixture for a predetermined period of time, the remainder of Solution A is added in equal portions, a measured amount of glacial acetic acid being added after each addition of Solution A. The additions are made at predetermined intervals of time. After the last addition, the coprecipitate is allowed to settle, the supernatant is decanted, the coprecipitate is slurried with a glycine buffer solution and then collected by filtration.

The glycine buffer solution (pH 2.6) used in washing the coprecipitates is prepared by dissolving 22.5 gms. of glycine and 17.55 gms. of sodium chloride in 2980 ml. of distilled water. An acidic solution is prepared by dissolving 8.2 ml. of concentrated hydrochloric acid in distilled water and diluting the solution to 1.0 liter in a volumetric flask. The glycine buffer solution is prepared by mixing 70.2 ml. of the saline glycine solution and 29.8 ml. of the acidic solution to give 100.0 ml. of a glycine buffer solution having pH 2.6.

In an alternate procedure, alkali metal carbonate, aspirin and tea are dissolved in water and the solution acidified to cause formation of coprecipitate, and thereafter the reaction mixture containing the coprecipitate and reaction liquor in the form of a slurry are spray dried together. In this procedure, salt formed by acidification of sodium acetylsalicylate, any free aspirin and any unreacted tea constituents are present along with the coprecipitate in the dried reaction residue, the sum of which constitutes the product in this procedure. Generally, the spray dried products containing the coprecipitate will contain 50–65 weight % total aspirin and 8 to 19 weight % total tea.

Bleeding Ulceration and Erosion

The coprecipitates prepared as described in the following examples were mixed with 10% disintegrating corn starch and the mixtures applied to multiple areas (2 to 3) of 5 cm.$^2$ each of gastric mucosa of anesthetized cats under individual glass observation cases and allowed to remain without drainage of fluids from the area for a prescribed length of time usually up to 60 minutes. Controls using aspirin and starch were also applied to an equal area of the gastric mucosa of the same cat, site selections being made at random. The tissue in each case, was examined microscopically and macroscopically for bleeding, erosion and ulceration, usually after 30 and 60 minute periods of residence time. Pharmacological results on bleeding are given at the end of each example.

Values relating to the significance of results (probability "P-Value") were determined by the "Student T-test" by means of a computerized program. Various factors which influence the standard error (S.E.), an important variant which figures heavily in P-Value determination are:

1. Sample size (number of drug sites) which in this instance is related to the number of cats used.

2. Variation in sensitivity between individual cats to the drug.

3. Variation in sensitivity of different areas within the cat's stomach to the drug.

Of these, 2 has contributed heavily in lowering the significance level (P = >0.05 or less than 95% significance) where only a few cats were used, (Ex. 5, 7, 8, 9 and 13 after 30 minutes) in which cases pronounced reduction in mean number of bleeding sites was observed.

Anti-Inflammatory Evaluation

In a controlled evaluation of anti-inflammatory effects of the aspirin-tea coprecipitate of Example 1 versus aspirin using two groups of 10 rats each, oral doses of 300 mg/kg of contained aspirin in the form of aspirin-tea coprecipitate or aspirin alone were administered orally to female rats weighing 125–150 g. via stomach tube 30 minutes prior to injection of carrageenan (0.2 ml. of a 1.0% suspension) into the plantar surface of the right hind paw of each animal. Equal volumes of saline were injected into the left paw. Three and one-half hours post drug administration, the rats were sacrificed, the hind paws removed and weighed. The reduction in edema was determined by comparing paw weights of the control and treated animals. At oral doses of 300 mg/kg, the aspirin-tea coprecipitate in its anti-inflammatory effects produced results comparable to aspirin; the former reducing foot edema by an overage of 44.9% in ten rats and aspirin reducing foot edema by an average of 40.2% in ten rats.

Blood Level Studies

Female Charles River rats weighing from 130–160 g. and starved for 48 hrs. prior to the study were dosed orally with 300 mg/kg aspirin-tea coprecipitate or aspirin and placed in groups of five animals each. At time intervals of 15, 30, 60, 120 and 240 minutes post-dosing, the rats were sacrificed in a carbon dioxide atmosphere. Blood samples were withdrawn via heart puncture through an opening in the chest cavity. A small amount of a 20% solution of potassium oxalate was used as anticoagulant. The blood samples (3.5–5.0 ml.) were centrifuged for ten minutes at 18,000 rpm. Plasma was removed and used for analysis of total salicylates. The analysis showed that the plasma levels of both compounds were very similar at all times, values having risen to 600–625 $\mu$g. salicylates per ml. of blood in both cases after 30 minutes where they remained until at least 240 minutes post dosage.

The following examples illustrate the methods by which the novel coprecipitates of the present invention are prepared. It is to be understood that the examples are merely illustrative and are not to be construed as limiting.

EXAMPLE 1

A cold solution (10° C.) of sodium acetylsalicylate was prepared using 25 gms. of aspirin, 8.65 gms. of sodium carbonate and 250 ml. of distilled water. The solution was stirred until complete solution occurred. A cold solution (5° C.) of tea was prepared by dissolving 6.25 gms. of instant tea in 750 ml. of distilled water. The two cold solutions were combined, maintained below 10° C. and stirred while 18.0 ml. of glacial acetic acid was added. After one hour an additional 25 ml. of glacial acetic acid was added in 5 ml. portions at 15 minute intervals. The mixture was stirred 20 minutes after the final acid addition, the coprecipitate collected by filtration after decanting the clear supernatant liquid and the coprecipitate thoroughly washed with 200 ml. of glycine buffer. The air dried material weighed 13 gms. Analysis of the coprecipitate showed in contained 95.5% aspirin, 3.67% tea constituent, 0.23% salicyclic acid and 0.6% water.

| | Pharmacology Mean No. of Bleeding Sites per Drug Application Site ± S.E. in 14 Cats. | |
|---|---|---|
| | 30 min. | 60 min. |
| Aspirin, 10 mg/5 cm$^2$ | 11.8 ± 2.6 | 24.55 ± 3.03 |
| Coprecipitate, 10 mg. contained aspirin/ 5 cm$^2$ | 4.05 ± 1.74 | 9.67 ± 2.08 |
| P Value | <0.025 | <0.001 |
| % Reduction in Mean No. of Bleeding Sites | 65.7 | 60.6 |

EXAMPLE 2

To seven liters of distilled water (10° C.) was successively added with stirring 363.3 gms. of sodium carbonate hydrate and 1050.0 gms. of aspirin. After solution of all solids had occurred, 262.6 gms. of instant tea was added. To 8.0 liters of stirred distilled water (10° C.) was added 2.64 liters of the aspirin-tea solution and then 200 ml. of glacial acetic acid; the solution was stirred one hour. There was then added eleven portions of 340 ml. each of the aspirin-tea solution, one portion of 320 ml. and four portions of 300 ml. After each addition of the aspirin-tea solution, glacial acetic acid was added, the first addition being 20 ml., each successive addition of acid being 10 ml. more than the previous addition. A period of 15 minutes occurred between each addition. Following the last 15 minute period the coprecipitate was allowed to settle, the supernatant liquid was decanted, the coprecipitate was washed with glycine buffer solution collected by filtration and air dried. The material weighed 815 gms. Analysis of the coprecipitate showed it contained 95.80% aspirin, 3.66% tea constituent, 0.14% salicylic acid and 0.40% water.

| | Pharmacology Mean No. of Bleeding Sites per Drug Application Site ± S.E. in 7 Cats. | |
|---|---|---|
| | 30 min. | 60 min. |
| Aspirin, 10 mg/5 cm$^2$ | 3.52 ± 1.07 | 14.88 ± 4.2 |
| Coprecipitate, 10 mg. contained aspirin/ 5 cm$^2$ | 0.67 ± 0.26 | 2.39 ± 0.88 |
| P Value | <0.025 | <0.01 |
| % Reduction in Mean No. of Bleeding Sites | 81 | 83.9 |

EXAMPLE 3

A cold solution (10° C.) of sodium acetylsalicylate was prepared by adding 34.6 gms. of sodium carbonate hydrate and 100 gms. of aspirin to 600 ml. of distilled water stirring until all solids had dissolved and using an additional 320 ml. of distilled water to wash down the walls of the container. Twenty-five gms. of instant tea was added with stirring until the tea dissolved. To 750. ml. of cold distilled water (5° C.) was added 250 ml. of the aspirin-tea solution and 20 ml. of glacial acetic acid. After a period of one hour the remaining aspirin-tea solution was added in 50 ml. portions with glacial acetic acid being added after each addition, the first amount being 4.0 ml. and increasing each addition by 1.0 ml.; a stirring period of 10 minutes occurred between each addition. The coprecipitate was allowed to settle, the supernatant was decanted, the coprecipitate was washed with glycine buffer solution and collected by filtration. After air drying, the product weighted 79.2 gms. Analysis of the coprecipitate showed it contained 95.3% aspirin, 4.17% tea constituent, 0.03% salicylic acid and 0.50% water.

| | Pharmacology Mean No. of Bleeding Sites per Drug Application Site ± S.E. in 12 Cats. | |
|---|---|---|
| | 30 min. | 60 min. |
| Aspirin, 10 mg/5 cm$^2$ | 9.03 ± 2.36 | 26.26 ± 3.13 |
| Coprecipitate, 10 mg. contained aspirin/ 5 cm$^2$ | 2.06 ± 1.18 | 7.94 ± 1.97 |
| P Value | <0.025 | <0.001 |
| % Reduction in Mean No. of Bleeding Sites | 77.2 | 69.8 |

EXAMPLE 3A

The procedure of Example 3 was repeated using the same amount and ratio of materials and careful pH measurements were made at 2° C. using a Beckman Zeromatic 553 pH meter Model 96.

pH of sodium acetylsalicylate-tea solution = 5.7
pH during coprecipitation (glacial acetic acid addition) = 4.2-4.39
Final pH = 4.19

EXAMPLE 4

Solution A (Sodium Acetylsalicylate Tea Solution)

A cold aqueous solution (10° C.) of sodium acetylsalicylate and tea (Solution A) was prepared using 895 ml. of water by adding successively with stirring 34.6 g. of sodium carbonate hydrate, 100.0 g. of aspirin, 47.0 g. of instant tea and 100 mg. of Dow Corning antifoam FG-10 emulsion. Complete solution of each ingredient was allowed to occur before the next was added.

Coprecipitation Step

The formation of the coprecipitate was carried out at 2° C. To 750 ml. of stirred water was added 250 ml. of Solution A, 40 ml. of glacial acetic acid and the mixture stirred for 1.0 hour. The remainder of Solution A was added in 50 ml. portions at ten minute intervals. Midway between each addition, glacial acetic acid was added, the first addition being 10 ml. and the amount of each successive addition being increased by 2.5 ml. The final addition of glacial acetic acid was 45 ml. Subsequent to the last addition of acid, the mixture was stirred 15 minutes. The coprecipitate was allowed to settle, the supernatant decanted and the coprecipitate washed several times with water by slurrying and decanting the wash water. After collecting the product on a filter, it was washed twice with glycine buffer and then air dried under a hood. The product weighed 79.1 g. The assayed produce contained 89.9% aspirin, 9.4% tea constituent, 0.2% salicylic acid and 0.5% moisture.

| | Pharmacology Mean No. of Bleeding Sites per Drug Application Site ± S.E. in 7 Cats. | |
|---|---|---|
| | 30 min. | 60 min. |
| Aspirin, 10 mg/5 cm² | 8.2 ± 2.9 | 23.3 ± 4.1 |
| Coprecipitate, 10 mg. contained aspirin/ 5 cm² | 0.8 ± 0.3 | 6.3 ± 1.7 |
| P Value | <0.025 | <0.001 |
| % Reduction in Mean No. of Bleeding Sites | 90.2 | 73.0 |

EXAMPLE 5

Solution A (Sodium Acetylsalicylate Tea Solution)

Solution A was prepared as in Example 4 at 1° C. using 8 liters distilled water, 389 g. sodium carbonate hydrate, 1,125 g. of 40 mesh aspirin, 450 g. of instant tea. No antifoam agent was used.

Preparation of the Coprecipitate

To 32.75 l. of distilled water (1° C.) in a 16 inches diameter open top stock pot having a capacity of 60 quarts was added all of the above Solution A prepared in this example. A 4 inches diameter marine propeller mounted 3 inches from the side of the pot was started and stirring continued for 45 minutes. Glacial acetic acid, 930 ml. was added on the surface of the stirred mixture at 1° C. at a point where foam was minimal to avoid entrapment of glacial acetic acid in the foam with consequent local over acidification, stirring being continued for 15 min. An additional 3.51 l. of glacial acetic acid was added in 9 portions at 15 minute intervals beginning with 270 ml. and increasing the size of each portion thereafter by 30 ml. and increasing the size of each portion thereafter by 30 ml. After the last addition, stirring was continued for 15 minutes and then after decanting most of the mother liquor, the coprecipitate was washed with 10 liters of aqueous hydrochloric acid solution having a pH of 2.6. The coprecipitate was collected on a filter and washed with 5 liters of the aqueous hydrochloric acid solution (pH 2.6). After air drying under air sweep in a hood the fine brownish colored material weighed 791 g. Analysis of the coprecipitate showed it contained 91.0% aspirin, 7.9% tea constituent, 0.1% salicyclic acid and 1.0% water. All phenolic constituents of tea were present in the coprecipitate as determined by paper chromatography. Same increase in proportion of thearubigen was evident.

| | Pharmacology Mean No. of Bleeding Sites per Drug Application Site ± S.E. in 4 Cats. | |
|---|---|---|
| | 30 min. | 60 min. |
| Aspirin, 10 mg/5 cm² | 5.0 ± 4.2 | 19.8 ± 5.8 |
| Coprecipitate 10 mg. contained aspirin/ 5 cm² | 0.5 ± 0.4 | 3.6 ± 2.2 |
| P Value | >0.05 | <0.025 |
| % Reduction in Mean No of Bleeding | | |

-continued

| | Pharmacology Mean No. of Bleeding Sites per Drug Application Site ± S.E. in 4 Cats. | |
|---|---|---|
| | 30 min. | 60 min. |
| Sites | 90 | 82 |

EXAMPLE 6

Solution A (Sodium Acetylsalicylate Tea Solution)

Sodium carbonate hydrate, 69.2 g. was dissolved in 3.7 l. of water at room temperature with stirring and thereafter the solution cooled to 10° C. Aspirin, 200 g. (40 mesh), was added with stirring to dissolve. The solution was cooled to 2° C and 64 g. of instant tea was added with stirring until dissolved.

Preparation of Coprecipitate

All of Solution A from above in this example was added with stirring to 2.1 of distilled water (2° C.) followed by addition of 160 ml. of glacial acetic acid and a 15 minute stirring period. Additional glacial acetic acid, 432 ml. was added in 8 portions at 15 minute intervals with stirring beginning with 40 ml. in size and increasing each portion by 4 ml. The mother liquor was decanted from the coprecipitate and washed several times to remove fines and mother liquor. The coprecipitate was collected on a filter and washed with glycine buffer (pH = 2.6) and air dried. Weight of the coprecipitate was 140.4 g. The coprecipitate contained 93.3 wt. % aspirin, 5.6 wt. % tea constituent, 0.5 wt. % salicylic acid and 0.6 wt. % water.

| | Pharmacology Mean No. of Bleeding Sites per Drug Application Site ± S.E. in 8 Cats (24 Sites) | |
|---|---|---|
| | 30 min. | 60 min. |
| Aspirin, 10 mg/5 cm² | 8.2 ± 3.0 | 20.0 ± 4.7 |
| Coprecipitate, 10 mg. contained aspirin/ 5 cm² | 1.83 ± 0.83 | 13.7 ± 4.6 |
| P. Value | <0.050 | >0.050 |
| % Reduction in Mean No. of Bleeding Sites | 78 | 31 |

Tablet Preparation (5 grains aspirin)

The coprecipitate obtained in Example 6 was tableted by compressing the following mixture on a 7/16 inch Std. Concave punch at 497 mg./tablet.

350 mg. coprecipitate
140 mg. Avicil PH 101™ (a)
3.5 mg. Guar gum
3.5 mg. Stearic acid
  (a) Avicil PH 101 is a microcrystalline cellulose (NF) molecular weight 30,000 to 50,000 and contains 4–6% moisture. Produced by Viscose Div. of FMC Corp., Marcus Hook, Pa.

Hardness was 8.0 kg. and thickness was 0.208. Desintegration time in an in vitro procedure was one minute.

The tablets were tested as above with the following results:

|  | Mean No. of Bleeding Sites per Drug Application Site ± S.E. in 8 Cats (18 sites). | |
|---|---|---|
|  | 30 min. | 60 min. |
| Aspirin, 10 mg/5 cm² | 6.6 ± 2.5 | 20.7 ± 4.1 |
| Tableted coprecipitate contained aspirin/ 5 cm² | 0.3 ± 0.2 | 5.8 ± 2.3 |
| P Value | <0.025 | <0.005 |
| Reduction in Mean No. of Bleeding Sites | 95 | 72 |

EXAMPLE 7

(Preparation of Decaffeinated Instant Tea)

Instant tea, 120 g. was stirred with one liter of chloroform for two hours, collected on a filter, washed with fresh chloroform and dried. The extracted instant tea powder was dissolved in 4 liters of water and passed over sodium cycle Amberlite to remove iron, manganese and calcium and then spray dried. The dried instant tea contained a trace amount of caffeine.

Solution A (Sodium Acetylsalicylate-Tea Solution)

Sodium carbonate hydrate, 34.6 g. was dissolved in 895 ml. water and 100 g. of (40 mesh) aspirin dissolved at room temperature with stirring. This solution of sodium acetylsalicylate was immediately placed in a water bath at 2° C. and nitrogen gas was bubbled through the solution for one hour. The decaffeinated tea prepared above, 47 g., was dissolved in the solution and antifoam agent Dow Corning EG-10 antifoam emulsion (25 drops) added while continuing to bubble nitrogen through the mixture. Total volume was 900 ml.

Coprecipitation Step

To 750 ml. water at 2° C. was added 250 ml. of cold Solution A. Glacial acetic acid, 40 ml. was added while continuing to sparge with nitrogen with stirring for one hour during which initial coprecipitate was formed. The remainder of Solution A was added in 50 ml. portions at 10 minute intervals, each Solution A addition being succeeded after 5 min. by additions of glacial acetic acid in increasing amount starting with a 10 ml. addition and increasing each addition by 2.5 ml., i.e., 2nd 12.5 ml., 3rd 15.0 ml. and so on. Thirteen additions of each were made. Total volume of Solution A used was 900 ml. and total volume of glacial acetic acid used was 365 ml. The coprecipitate was collected on a filter and washed twice with glycine buffer solution of pH 2.6. Yield of coprecipitate was 67.8 g. Analysis of the coprecipitate showed it contained 94.0 wt % aspirin, 5.1 wt. % tea constituent, 0.2 wt. % salicylic acid and 0.7 wt. % water.

| Pharmacology | Mean No. of Bleeding Sites per Drug Application Site ± S.E. in 3 Cats | |
|---|---|---|
|  | 30 min. | 60 min. |
| Aspirin, 10 mg/5 cm² | 7.7 ± 2.5 | 25.7 ± 4.2 |
| Coprecipitate, 10 mg. contained aspirin/ 5 cm² | 3.1 ± 2.2 | 11.0 ± 3.1 |
| P Value | >0.05 | <0.010 |
| % Reduction in Mean No. | | |

-continued

| | Pharmacology Mean No. of Bleeding Sites per Drug Application Site ± S.E. in 3 Cats | |
|---|---|---|
|  | 30 min. | 60 min. |
| of Bleeding Sites | 60 | 57 |

EXAMPLE 8

(Sodium Acetylsalicylate Solution)

A cold (10° C.) solution of sodium acetylsalicyclic acid was prepared using 50 g. of 40 mesh aspirin, 17.3 g. of sodium carbonate and 440 ml. of water. The solution was stirred until complete solution occurred.

Tea Infusion

To 800 ml. of boiling water was added 50 g. of tea leaf (Pekoe and Orange Pekoe blend) and the mixture was steeped for 15 min., after which it was strained through a cloth. The residual leaf was washed with about 200 ml. hot distilled water and the washing combined with the main tea solution.

Preparation of Coprecipitate

All of the foregoing tea infusion was cooled to <5° C. and to it was added all of Solution A keeping the temperature at about 5° C. with stirring. To the tea and sodium acetylsalicylate solution was added 25 ml. of glacial acetic acid. After stirring for one hour, thirteen additions of 6 ml. portions of glacial acetic acid were added at 15 minute intervals. Total glacial acetic acid added was 103 ml. After settling, decanting, filtering and washing the solids with glycine buffer solution (pH 2.6) and air drying the coprecipitate product weighted 31 g. Analysis of the coprecipitate showed it contained 94.6% aspirin, 4.9% tea constituent, 0.0% salicylic acid and 0.5% water.

| | Pharmacology Mean No. of Bleeding Sites per Drug Application Site ± S.E. in 2 Cats. | |
|---|---|---|
|  | 30 min. | 60 min. |
| Aspirin, 10 mg/5 cm² | 6.8 ± 3.6 | 32.3 ± 8.4 |
| Coprecipitate, 10 mg. contained aspirin/ 5 cm² | 1.0 ± 0.4 | 41.0 ± 3.7 |
| P Value | >0.05 | >0.05 |
| % Reduction in Mean No. of Bleeding Sites | 85 | none |

EXAMPLE 9

Fractionation of Tea-Tannin from Instant Tea By Adsorption-Desorption

Instant tea, 300 g. was dissolved in 3 liters of water at 86° C. Polyclar AT powder, 120 g., which is a high-molecular weight cross-linked form of polyvinyl pyrrolidone product sold by the GAF Corporation prepared under U.S. Pat. No. 3,117,004, was added to the tea solution with stirring until the mixture had cooled to room temperature. The mixture was filtered and the solids suspended in about 700 ml. of 50% dimethylformamide (DMF) 50% water solution by volume. The mixture was filtered and washed with 500 ml. more 50—50 DMF solution. Water and dimethylformamide were removed on a rotary evaporator after which the residue was dissolved in 700 ml. of distilled water and spray dried. Yield of product was 31.1 g. No caffeine could be detected by thin layer chromatography.

Solution A (Sodium Acetylsalicylate-Tea Solution)

An aqueous solution (Solution A) was prepared using 712.5 ml. of distilled water by adding successively with stirring 6.47 g. of sodium carbonate hydrate, 18.75 g. aspirin, 3.75 g. tea as prepared above. Complete solution of each ingredient was allowed to occur before the next was added. The solution was cooled to 2° C.

Coprecipitation Step (Decaffeinated Product)

To a cold (2° C.) stirred Solution A was added 15.5 ml. of glacial acetic acid followed at 15 minute intervals by 9 successive additions of glacial acetic acid beginning with 4.5 ml. and increasing each successive addition by 0.5 ml. Total glacial acetic acid added was 74 ml. After decanting, washing and drying the coprecipitate weighed 11.5 g. The assayed product contained 93.6% aspirin, 5.2% tea constituent, 0.3% salicylic acid and 0.9% moisture. No caffeine could be detected by thin layer chromatography.

| | Pharmacology Mean No. of Bleeding Sites per Drug Application Site ± S.E. in 3 Cats. | |
|---|---|---|
| | 30 min. | 60 min. |
| Aspirin, 10 mg/5 cm$^2$ | 10.6 ± 6.3 | 18.9 ± 6.3 |
| Coprecipitate, 10 mg. contained aspirin/ 5 cm$^2$ | 0.3 ± 0.2 | 1.2 ± 0.6 |
| P Value | >0.05 | <0.025 |
| % Reduction in Mean No. of Bleeding Sites | 97.1 | 93.5 |

EXAMPLE 10

Solution 1

(Sodium Acetylsalicylate Solution)

To one liter of distilled water was added 34.6 g. of sodium carbonate hydrate and with cooling (2° C.) and stirring was added 100 g. of 40 mesh aspirin.

Solution 2

(Instant Tea Solution)

To 1.85 liters of distilled water was added 44 g. of instant tea.

Coprecipitation Step

Solutions 1 and 2 were cooled (2° C.) and mixed (Solution A) and 10 ml. of an aqueous solution containing 100 mg. of Dow Corning antifoam FG-10 emulsion was added. To the mixture was added 80 ml. of glacial acetic acid with stirring for one hour after which time no precipitate was evident on visual observation. Eight ml. of glacial acetic acid was added with stirring for 15 min. Ten more additions of glacial acetic acid were made increasing over the 8 ml. by 2 ml. each addition. After addition was complete the pH of the reaction mixture was 3.75. Total glacial acetic acid added was 278 ml. The mixture was allowed to settle, decanted and the coprecipitate washed with glycine buffer solution (pH 2.6) and air dried. The product weighed 63.4 g. Analysis of the coprecipitate showed it contained 92.9% aspirin, 0.05% salicylic acid, 5.85% tea constituent, and 1.2% water.

EXAMPLE 11

The coprecipitation procedure of Example 10 was repeated ten times using the same amounts and materials and the same sequence of addition. Instead of washing as in Example 10, the coprecipitate was washed 3 times with distilled water followed by washing two times with glycine buffer solution (pH 2.6). Total recovery from the 10 batches was 650 g. after drying. Analysis of the coprecipitate showed it contained 92.3% aspirin, 5.7% tea constituent, 0.3% salicylic acid and 1.7% water.

| | Pharmacology Mean No. of Bleeding Sites per Drug Application Site ± S.E. in 8 Cats. | |
|---|---|---|
| | 30 min. | 60 min. |
| Aspirin, 10 mg/5 cm$^2$ | 9.6 ± 2.1 | 25.9 ± 4.5 |
| Coprecipitate, 10 mg. contained aspirin/ 5 cm$^2$ | 1.0 ± 0.5 | 8.5 ± 2.5 |
| P Value | <0.001 | <0.005 |
| % Reduction in Mean No. of Bleeding Sites | 89.5 | 82.6 |

EXAMPLE 12

Solution A (Sodium Acetylsalicylate-Tea Solution)

Utilizing the procedure of Example 4, an aqueous solution of sodium acetylsalicylate and tea (Solution A) at 2° C. was prepared using 18 liters of distilled water, 692 g. of sodium carbonate hydrate, 2000 g. of aspirin and 1200 g. of instant tea. No antifoam agent was used.

Coprecipitation Step

To 15 liters of cold (2° C.) distilled water was added 5 liters of Solution A and one liter of glacial acetic acid all at 2° C. The mixture was stirred for one hour. The remainder of Solution A was added in fifteen one liter portions at 10 minute intervals while alternately adding glacial acetic acid five minutes after each Solution A addition, said glacial acetic acid being added in 200 ml. amount on the first addition and the amount being increased by 40 ml. on each successive addition thereafter. Total glacial acetic acid added was 8.2 liters. After 15 minutes stirring time past the last addition, the mixture was allowed to settle and the supernatant was decanted and the coprecipitate was washed with distilled water several times to remove fines. The coprecipitate was collected on a filter and washed with glycine buffer solution (pH 2.6) and air dried under a hood. The product weighed 1,115 g. Analysis of the coprecipitate showed it contained 94.9% aspirin, 4.19% tea constituent, 0.20% salicylic acid and 0.71% water.

| | Pharmacology | |
|---|---|---|
| | Mean No. of Bleeding Sites per Drug Application Site ± S.E. in 7 Cats. | |
| | 30 min. | 60 min. |
| Aspirin, 10 mg/5 cm² | 4.8 ± 1.8 | 23.9 ± 4.0 |
| Coprecipitate, 10 mg. contained aspirin/ 5 cm² | 0.5 ± 0.3 | 5.6 ± 1.3 |
| P Value | <0.05 | <0.001 |
| % Reduction in Mean No. of Bleeding Sites | 88.8 | 76.6 |

EXAMPLE 13

Solution 1

(Sodium Acetylsalicylate Solution)

A solution of 8.65 g. of sodium carbonate hydrate was dissolved in water and cooled to 10° C. Aspirin, 25 g. of 40 mesh size, was added with stirring until dissolved.

Solution 2

(Soluble Tea Cream Solution)

Five and one-half g. of tea cream which was obtained by filtering and cooling a hot infusion of tea leaves to obtain an insoluble complex of caffeine and theoflavins and thearubigins was oxidized and solubilized with basic hydrogen peroxide solution according to the procedure of U.S. Pat. No. 3,151,985 and was added to 200 ml. of water with stirring. Insoluble material was centrifuged out at 4000 rpm. for 30 minutes. The tea cream solution was decanted off and the solids discarded.

Solution A (Sodium Acetylsalicylate-Tea Solution)

Solutions 1 and 2 were combined to form a sodium acetylsalicylate tea cream solution (Solution A).

Coprecipitation Step

To Solution A was added 725 ml. of distilled water and the resulting solution was cooled to 2° C. Eighty ml. of glacial acetic acid was added with stirring and stirring continued for one hour. Additional acetic acid in ten 20 ml. portions was added at 15 minute intervals. Stirring was continued for 15 min. after the last addition of acid. The mixture was allowed to settle and the supernatant decanted. The solid was washed with distilled water and collected on a filter and washed with glycine buffer solution. After drying in air under a hood the product weighed 12.4 g. Analysis of the coprecipitate showed it contained 93.3% aspirin, 5.9% tea constituent, 0.3% salicylic acid and 0.5% water.

| | Pharmacology | |
|---|---|---|
| | Mean No. of Bleeding Sites per Drug Application Site ± S.E. in 5 Cats. | |
| | 30 min. | 60 min. |
| Aspirin, 10 mg./5 cm² | 7.6 ± 3.3 | 19.0 ± 4.7 |
| Coprecipitate, 10 mg. contained aspirin/ 5 cm² | 1.3 ± 0.8 | 9.7 ± 4.4 |
| P Value | >0.05 | >0.05 |
| % Reduction in Mean No. of Bleeding Sites | 83 | 54 |

EXAMPLE 14

An aqueous solution of sodium acetylsalicylate was prepared using 50.0 g. of aspirin, 17.3 g. of sodium carbonate hydrate and 1,425 ml. water at room temperature (25° C.). After solution of all solids had occurred, 15.0 g. of instant tea was added while stirring at room temperature (25° C.). To the aqueous solution was added with rapid stirring in about 5–30 seconds 140 ml. of 2N $H_2SO_4$ and stirring was continued for 15 minutes at room temperature. The pH of the reaction mixture was after acidification was 2.6. The aqueous slurry under constant agitation was immediately thereafter spray dried in a Nichols portable spray drier (Minor Type 53) using a Nitro atomizer having a rotational speed of 31,000 r.p.m. The operating temperatures were 165° C. on the inlet side and exhaust temperatures were just under 80° C. The spray dried product weighed 76.2 g. and was light tan in color. Analysis of the spray dried product containing the coprecipitate showed it contained 56% aspirin, 0.32% salicylic acid and 1.8% water. Tea content of the spray dried product is approximately 18.8 weight %.

| | Pharmacology | |
|---|---|---|
| | Mean No. of Bleeding Sites per Drug Application Site ± S.E. in 4 Cats. | |
| | 30 min. | 60 min. |
| Aspirin, 10 mg/5 cm² | 13.6 ± 4.8 | 31.8 ± 6.6 |
| Spray Dried Reaction Product containing coprecipitate,10 mg. contained aspirin/ 5 cm² | 0.9 ± 0.4 | 8.6 ± 4.1 |
| P Value | <0.025 | <0.01 |
| % Reduction in Mean No. of Bleeding Sites | −93 | −73 |

EXAMPLE 15

An aqueous solution of sodium acetylsalicylate was prepared using 100.0 g. of aspirin, 34.6 g. of sodium carbonate hydrate and 1,425 ml. water at room temperature (25° C.). After solution of all solids had occurred, 30.0 g. of instant tea was added while stirring at room temperature. To the aqueous solution was added with rapid stirring in less than 30 seconds 280 ml. of 2N $H_2SO_4$ and stirring was continued for 15 minutes at room temperature. The pH of the reaction after acidification was 3.3. The aqueous slurry was immediately thereafter spray dired in a Nichols portable spray drier (Minor Type 53) using a Nitro atomizer having a rotational speed of 31,000 r.p.m. The operating temperatures were about 165° C. on the inlet side and less 80° C. on the exhaust side. Weight of the spray dried product was 158.5 g. Analysis of the spray dried product containing the coprecipitate showed it contained 55% aspirin, 0.64% salicylic acid and 2.7% water. Tea content of the spray dried product is approximately 18.8%.

| Pharmacology | | |
|---|---|---|
| | Mean No. of Bleeding Sites per Drug Application Site ± S.E. in 5 Cats | |
| | 30 min. | 60 min. |
| Aspirin, 10 mg/5 cm² | 5.6 ± 3.4 | 15.1 ± 4.5 |
| Spray Dried Reaction Product containing coprecipitate, 10 mg. contained aspirin/ 5 cm² | 0.2 ± 0.2 | 4.8 ± 2.0 |
| P Value | >0.05 | <0.05 |
| % Reduction in Mean No. of Bleeding Sites | −96 | −68 |

Tablets were prepared from the following mix.

| | |
|---|---|
| Spray dried Reaction product | 145.0 g. |
| Avicil PH 101 (microcrystalline cellulose) | 29.0 g. |
| Guar Gum | 3.9 |
| Stearic acid | 0.025 |
| Cab-O-Sil M-5 (finely divided silica) | 0.025 |
| Stear-O-Wet-C (calcium stearate and sod. lauryl sulfate) | 1.23 |

The spray dried reaction product was slugged on a Stoke's Model F tablet machine using a ¾ inch FF, BE punch. Slugs were sized through a No. 14 hand screen and blended with other ingredients. Tablets were formed with a hand punch. Weight of tablets was 730 mg. each and thickness 0.250 inch. Tablets disintegrate rapidly in artificial gastric juice at 37° C. The tableted material was tested in cats as follows.

| Pharmacology | | |
|---|---|---|
| | Mean No. of Bleeding Sites per Drug Application Site ± S.E. in 10 Cats. | |
| | 30 min. | 60 min. |
| Bayer Aspirin Tablet (5 grains) | 11.3 ± 5.2 | 35.4 ± 8.5 |
| Tableted Spray Dried Reaction Product as per above (5 grains) | 0.7 ± 0.5 | 2.0 ± 1.8 |
| P Value | >0.05 | <0.005 |
| % Reduction in Mean No. of Bleeding Sites | −94 | −94 |

Formulation and Administration

The novel anti-inflammatory coprecipitates of the present invention can be formulated readily into pressed or coated tablets, they can be encapsulated and they can be formulated into other pharmaceutical dosage forms such as liquid suspensions and powders. Any of the various pharmaceutically acceptable pharmaceutical carriers can be used including, for example, fillers such as cellulose, corn starch, lactose, and dicalcium phosphate, and disintegrating agents such as maize and starch, and lubricants such as talc and stearic acid. The methods and techniques which will be most suitable in formulating the present compositions will be readily apparent to those skilled in the art.

Typical oral dosages of the compositions of this invention will vary within rather wide limits. For example, in the case of a tablet containing 340 mg. of an aspirin-tea coprecipitate, or an equivalent amount of aspirin contained in a spray dried product, a typical oral dosage for an adult will be up to two tablets every four hours as required. In the case of a tablet containing about 680 mg. of said coprecipitate of aspirin and tea, a typical oral dosage for an adult will be up to one tablet every four hours as required. In the case of children age 6 to 12, or in the case of debilitated patients, smaller doses may, of course, be more appropriate. On the other hand, in the case of patients experiencing severe discomfort due to pain, more frequent administration of the preparations may be prescribed. It should be fully understood, therefore, that the typical dosages mentioned herein are exemplary only and that they do not to any extent limit the scope of the practice of the present invention.

ANALYTICAL METHODS

Chromatographic Analysis for Acetylsalicylic Acid and Salicylic Acid (Relative Peak Height Method).

INSTRUMENT AND TECNHIQUE.

A gas chromatograph Micro Tek-220 having a hydrogen flame detector and a column as follows:
4' × 4 mm. 2% OV-1 + 1% OV-17 on 100/120 mesh Gas-Chrom Q was used. Temperatures were as follows: oven −140° C. (Inlet 225° C; Detector 225° C.). Gas flows were: Air-1.2 cfh., $H_2$ - 40 ml/min., He - 60 ml/min. The following retention times were observed:
Salicylic Acid - 2.3 min.
Aspirin - 3.1 min.
Butylparaben - 9.0 min.

REAGENTS AND STANDARDS

1. Internal Standard Solution. Prepare a solution of butylparaben equivalent to 10 mg/ml. in chloroform.
2. Silylating Agent. Pipet 20 ml. BSA and 10 ml. TMCS into a 100 ml. volumetric flask and dilute with chloroform.
3. Reagent Blank. Combine 2 ml. of internal standard solution, 2 ml. of silylating agent and 2 ml. of chloroform in a 10 ml. volumetric flask.
4. Aspirin Standard. Weigh 162 mg. aspirin into a 25 ml. volumetric flask and dilute to volume with chloroform. In a 10 ml. volumetric flask, combine 2 ml. of this solution, 2 ml. of internal standard solution and 2 ml. of silylating agent.
5. Salicylic Acid Standard: Prepare a solution of salicylic acid containing 0.05 mg/ml in chloroform. Combine 2 ml. of internal standard solution and 2 ml. of silylating agent in a 10 ml. volumetric flask.

PROCEDURE.

Reagent Blank: Inject an appropriate volume into the chromatograph and record the chromatogram. Obtain the peak height H for the unknown from BSA which elutes directly under salicylic acid and determine Rb where $$Rb = \frac{H \text{ unknown}}{H \text{ butylparaben}}$$

Samples: Weight an amount of sample equivalent to 162 mg. aspirin and transfer to a 25 ml. volumetric flask with about 15 ml. chloroform. Shake for 30 minutes and dilute to volume. Pipet 2 ml. sample solution into a 10 ml. volumetric flask containing 2 ml. internal standard. Add 2 ml. silylating agent and allow to reset for 15 minutes. Inject an appropriate volume of standards and samples into the chromatograph and record the chromatograms. Obtain peak heights, H for salicylic acid, aspirin and butyparaben and determine Rs for each standard, where $$Rs = \frac{H \text{ aspirin or salicylic acid}}{H \text{ butylparaben}}$$

Ru values are determined similarly for the samples. Calculate % aspirin as follows:

$$\% \text{ ASA} = \frac{Ws \; Ru \times 100}{Wu \; Rs}$$

where Wu = weight of sample, Ws = weight of standard. Calculate % salicylic acid as follows:

$$\% \text{ Sal A} = \frac{Ws \; (Ru - Rb) \times 100}{Wu \; (Rs - Rb)}$$

DISCUSSION.

Separate standards must be prepared for aspirin and salicylic acid because aspirin contains enough salicylic acid to interfere with determination of salicylic acid at extremely low levels. The salicylic acid standard described represents 0.1% salicylic acid. If the sample contains a much greater amount of salicylic acid, standards of the desired concentration may be prepared in the same manner. Studies show that a calibration curve for salicylic acid standards of various concentrations is linear.

The unknown peak under salicylic acid increases with time, so the salicylic acid standard must be prepared the same day as the samples. It is essential that the same silylating agent be used throughout an assay.

Water Analysis. Water in coprecipitates was determined by the Karl Fischer method.

Tea Constituents. Tea constituents were determined by difference, i.e., 100 - % ASA - % SaL A - % $H_2O$.

What is claimed is:

1. A process for the preparation of a water insoluble aspirin-tea coprecipitate wherein said coprecipitate is comprised of 85–98 weight % aspirin and 2–15 weight % tea constituent which comprises mixing aspirin, tea and a base in water, said base being an amount to form a soluble acetyl salicylate, the resulting solution containing from about 2 to about 7 weight % acetyl salicylate and from about 0.3 to about 3.5 weight % tea, acidifying the solution at a temperature of from about −2° to about 25° C. and to a pH of from about 4.2 to about 2.6 to cause formation of the coprecipitate and recovering the coprecipitate.

2. A process in accordance with claim 1 wherein the tea used is instant tea.

3. A process in accordance with claim 1 wherein the tea used is decaffeinated instant tea.

4. A process in accordance with claim 1 wherein the tea used is solubilized tea cream.

5. A process in accordance with claim 1 wherein the coprecipitate is separated from the reaction liquor, washed with water or a buffer solution having a pH of about 2.6 and said coprecipitate dried by conventional means.

6. The product of the process of claim 5.

7. The process of claim 5 wherein the tea used is instant tea.

8. The product of the process of claim 7.

9. The process of claim 5 wherein the tea used in decaffeinated instant tea.

10. The product of the process of claim 9.

11. The process of claim 5 wherein the tea used in solubilized tea cream.

12. The product of the process of claim 11.

13. A process in accordance with claim 1 wherein the coprecipitate is recovered by spray drying, the spray dried product containing from about 50 to about 65 weight % aspirin, from about 8 to about 19 weight % tea constituent and the salt formed by acidification.

14. The product of the process of claim 13.

15. A process in accordance with claim 13 wherein the tea used is instant tea.

16. The product of the process of claim 15.

17. A process in accordance with claim 13 wherein the tea used is decaffeinated instant tea.

18. The product of the process of claim 17.

19. A process in accordance with claim 13 wherein the tea used is solubilized tea cream.

20. The product of the process of claim 19.

21. A composition useful for treating inflammation in warm blooded animals comprising (a) a coprecipitate of aspirin and tea constituent of claim 5 and (b) a pharmaceutical carrier therewith.

22. A composition useful for treating inflammation in warm blooded animals comprising (a) the spray dried product of claim 13 and (b) a pharmaceutical carrier therewith.

23. A method of treating inflammation in warm blooded animals which comprises administering to said animals an anti-inflammatory amount of the product of the process of claim 5.

24. A method of treating inflammation in warm blooded animals which comprises administering to said animals an anti-inflammatory amount of the product of the process of claim 13.

* * * * *